(12) United States Patent
Banerjee et al.

(10) Patent No.: US 10,656,515 B2
(45) Date of Patent: May 19, 2020

(54) PHOTOCHROMIC METAL ORGANIC FRAMEWORKS FOR INKLESS AND ERASABLE PRINTING

(71) Applicant: Council of Scientific & Industrial Research, Rafi Marg New Delhi (IN)

(72) Inventors: Rahul Banerjee, Pune (IN); Bikash Garai, Pune (IN); Arijit Mallick, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 24 days.

(21) Appl. No.: 15/527,960

(22) PCT Filed: Sep. 30, 2015

(86) PCT No.: PCT/IN2015/050125
§ 371 (c)(1),
(2) Date: May 18, 2017

(87) PCT Pub. No.: WO2017/025976
PCT Pub. Date: Feb. 16, 2017

(65) Prior Publication Data
US 2018/0143525 A1 May 24, 2018

(30) Foreign Application Priority Data
Aug. 11, 2015 (IN) .......................... 2460/DEL/2015

(51) Int. Cl.
*G03C 1/735* (2006.01)
*C07D 471/04* (2006.01)
*B41M 5/00* (2006.01)
*C07D 471/06* (2006.01)

(52) U.S. Cl.
CPC ............ *G03C 1/735* (2013.01); *B41M 5/00* (2013.01); *C07D 471/04* (2013.01); *C07D 471/06* (2013.01)

(58) Field of Classification Search
None
See application file for complete search history.

(56) References Cited

U.S. PATENT DOCUMENTS
2006/0251988 A1  11/2006  Iftime et al.

FOREIGN PATENT DOCUMENTS
EP  2003493  12/2008
EP  2003494  12/2008

OTHER PUBLICATIONS

Cairns. Journal of the American Chemical Society, 2008, 130, 1560-61 (Year: 2008).*
Han. Chemical Communications, 2013, 49, 406-408, supporting information (Year: 2013).*
Cotton, Advanced inorganic Chemistry, 1999, inside cover (Year: 1999).*
Zhuang, et al., "Patterned Deposition of Metal-Organic Frameworks Onto Plastic, Paper, and Textile Substrates by Inkjet Printing of a Precursor Solution", Advanced Materials, 2013, pp. 1-5.
Kundu, et al., "Alkali earth metal (Ca, Sr, Ba) based thermostable metal-organic frameworks (MOFs) for proton conduction", Chem. Commun,. 2012, No. 48, pp. 4998-5000.
Han, et al., "A novel photochromic calcium-based metal-organic framework derived from a naphthalene diimide chromophore", Chem. Commun., 2013, No. 49, pp. 406-408.
Zhang, et al., "Structure Design of Naphthalimide Derivatives: Toward Versatile Photoinitiators for Near-UV/Visible LEDs, 2D Printing, and Water-Soluble Photoinitiating Systems", American Chemical Society, pp. A-J.
International Search Report for PCT/IN2015/050125, dated Jan. 15, 2016.
Written Opinion for PCT/IN2015/050125, dated Jan. 15, 2016.

* cited by examiner

*Primary Examiner* — Noble E Jarrell
(74) *Attorney, Agent, or Firm* — Nixon Peabody LLP; Jeffrey L. Costellia

(57) ABSTRACT

The present invention disclose photochromic metal organic frameworks (MOFs) containing photochromic 1,4,5,8-naphthalenediimide (NDI) core and metal ions selected from Mg, Ca or Sr. The developed MOFs find application in inkless and erasable printing wherein they retain the photogenerated colour for a prolonged period of time so that the printed content remains legible/readable for reasonable time.

12 Claims, 14 Drawing Sheets

Figure 1:
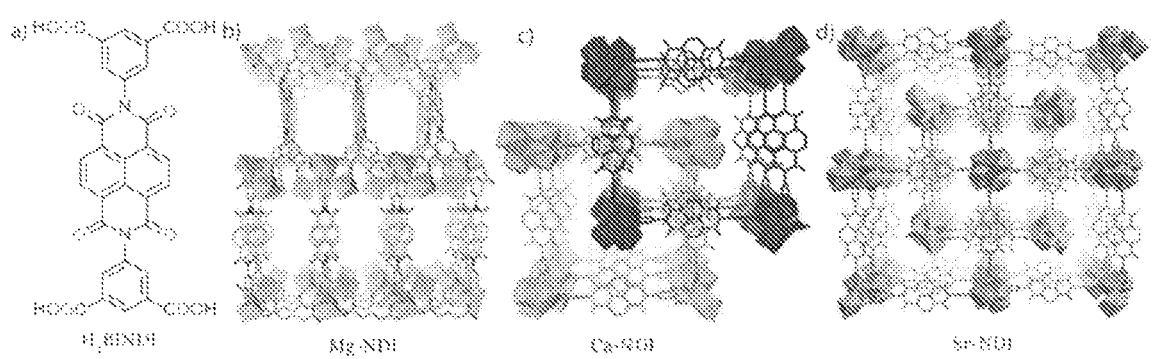

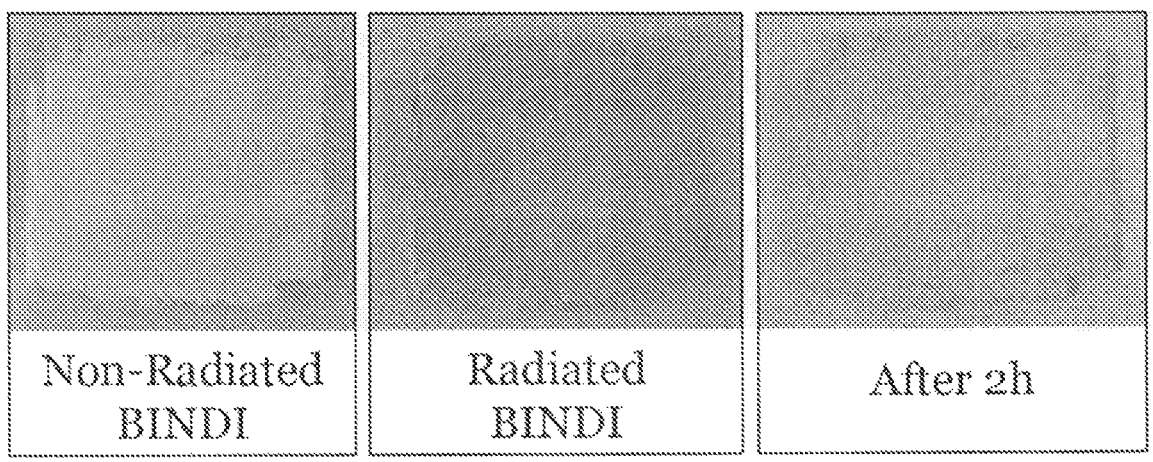
Figure: 13

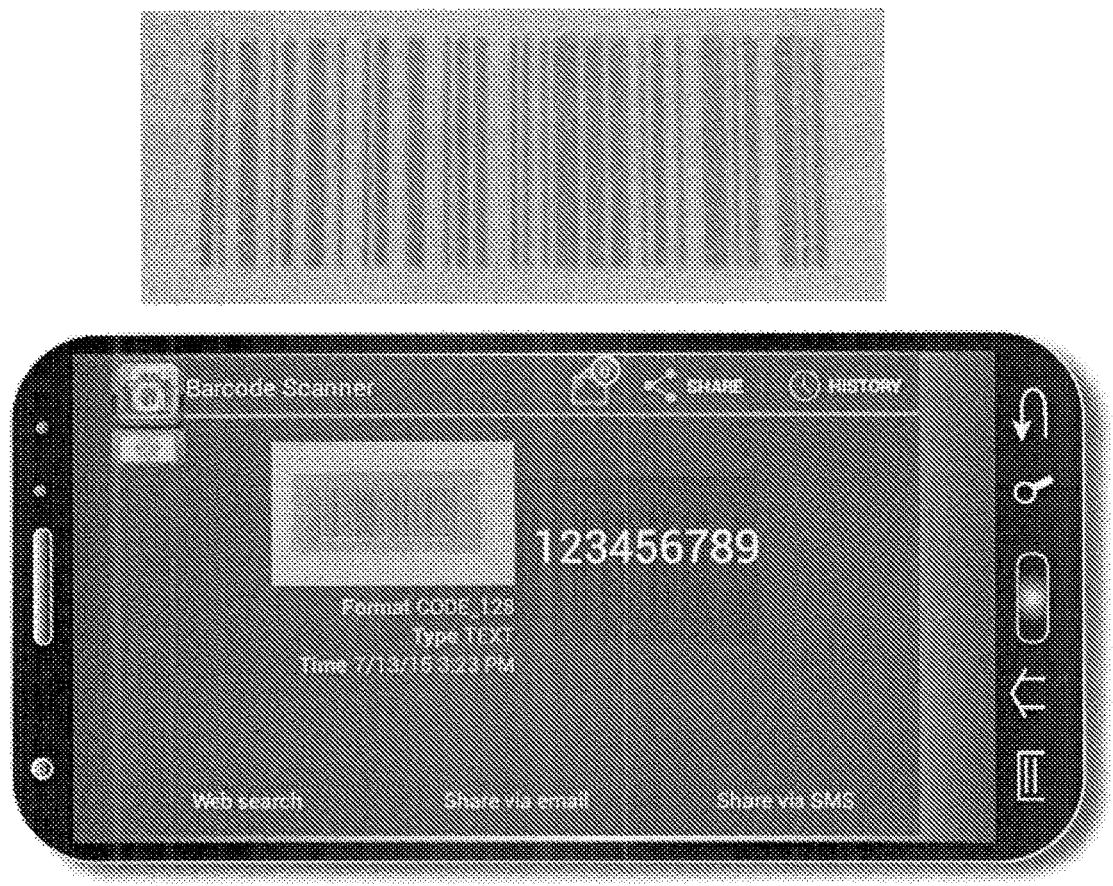
Figure: 14

PHOTOCHROMIC METAL ORGANIC FRAMEWORKS FOR INKLESS AND ERASABLE PRINTING

FIELD OF THE INVENTION

The present invention relates to photochromic Metal-Organic Frameworks for use in Inkless and Erasable Printing. More particularly, the present invention relates to metal organic frameworks (MOFs) containing photochromic 1,4,5,8-naphthalenediimide (NDI) core and metal ions selected from Mg or Sr and application thereof in inkless and erasable printing.

BACKGROUND OF THE INVENTION AND DESCRIPTION OF PRIOR ART

Although, recycling of paper saves energy, reduces pollution, preserves trees and conserves landfill space, yet the same is a complicated and disordered process as it involves the use of caustic chemicals and produces harmful by-products and emissions. The paper recycling process requires the removal of printing inks from the used paper, which is really problematic because it is not really ink but rather a plastic polymer which the printer or copier burns onto the paper. The removal of these inks requires chemicals that are much more corrosive than standard de-inking chemicals. Moreover, printing inks contain heavy metals and other compounds that require strong solvents to remove these compounds. Furthermore, when recycling facilities remove inks from paper, the waste, which includes the metals used in printing inks, such as copper, lead, zinc, chromium and cadmium makes its way into the water stream. Therefore, the paper recycling industries are struggling to devise more eco-friendly and greener techniques so as to eliminate the sludge formed during the de-inking process.

In light of the above, the best way to reduce paper-related pollution and consumption of energy is to cut back on paper consumption, which will decrease the demand for new or recycled paper. However, this is not possible due to the increase in printing on paper owing to the global civilization. In most of the cases, paper is printed to serve temporary jobs, for example, daily newspapers and after the consumption, it becomes useless and is thrown away as waste paper. Thus, tons of papers are wasted each day at the cost of thousands of trees, causing global deforestation and lots of associated environmental problems. As mentioned above, the conventional way to reduce the paper waste is to recycle the used paper and produce fresh papers; however, the chemicals used for this recycling process should be environmentally and economically acceptable.

Therefore, inkless and erasable printing appears to be an important and key solution for reducing the deforestation and related problems arising from the global paper manufacture and recycling. Photochromic materials are capable of changing colour when exposed to light and such photochromic materials contain spiropyran, diarylethene and azobenzene or redox active cores in their structures which are responsible for the colour change when exposed to light. These photochromic materials have been extensively used for making photochromic glasses, lenses, and filters because of their interesting reversible colour change property. Moreover, these materials have also been proposed for applications like erasable and inkless printing, 3D data storage, etc. However, conventional photochromic materials, as mentioned above, have short lifetime and return to the initial colour within a few minutes of excitation, making them inappropriate for the inkless erasable printing applications.

As is evident from the foregoing, the prior art fails to address the following necessary conditions which are essential to design a practical erasable printing media which include: (i) their ability to retain the photogenerated colour for a prolonged period of time so that the content remains legible/readable; (ii) the reversibility of this colour change so that the same paper can be used for multiple cycles, and (iii) the intactness of the colour in presence of paper contents.

Article titled "A novel photochromic calcium-based metal-organic framework derived from a naphthalene diimide chromophore" by L Han et al. published in Chem. Commun., 2013,49, pp 406-408 reports a novel 3D calcium-based metal-organic framework based on a naphthalenediimide chromophore which displays a unique doubly interpenetrated 7-connected net with total point symbol of $\{3 6 \cdot 4 9 \cdot 5 6\}$. The MOF has excellent thermal stability and reversible photochromic properties varying from yellowish to dark green. The Compound $[Ca_2(BIPA-TC)(DMF)_4]\cdot_2DMF$ was obtained as yellowish block crystals via a solvothermal reaction of H4BIPA-TC and $Ca(NO_3)24H_2O$ in DMF at 100° C. for 72 h. However, the article does not describe any attempt to use the photochromic property of the materials as a medium for inkless and erasable printing.

Article titled "Alkali earth metal (Ca, Sr, Ba) based thermostable metal-organic frameworks (MOFs) for proton conduction" by T Kundu et al. published in Chem. Commun., 2012, 48, pp 4998-5000 reports three new alkaline earth metal based MOFs that have been synthesized by using 4,4'-sulfobisbenzoic acid (SBBA) and alkaline earth metal salts $M(NO3)2$, M=Ca, Sr, Ba. These MOFs exhibit interesting structural diversity, variable chemical stability as well as proton conductivity. However, the article doesn't deal with any photochromic property of the materials (MOFs), nor with the application as inkless and erasable printing.

Article titled "Structure Design of Naphthalimide Derivatives: Toward Versatile Photoinitiators for Near-UV/Visible LEDs, 3D Printing, and Water-Soluble Photoinitiating Systems" by J Zhang et al. published in Macromolecules, Apr. 3, 2015, 48 (7), pp 2054-2063 reports seven naphthalimide derivatives (NDP1-NDP7) with different substituents as versatile photoinitiators (PIs), and some of them when combined with an iodonium salt (and optionally N-vinylcarbazole) or an amine (and optionally chlorotriazine) are expected to exhibit an enhanced efficiency to initiate the cationic polymerization of epoxides.

Article titled "Patterned Deposition of Metal-Organic Frameworks onto Plastic, Paper, and Textile Substrates by Inkjet Printing of a Precursor Solution" by J L Zhuang et al. published in Adv Mater., 2013; 25(33), pp 4631-4635 reports that inkjet printing of metal-organic frameworks permits their larger area, high-resolution deposition in any desired pattern, even in the form of gradients or shades.

U.S. Patent application no. 20080311495 discloses a photochromic material, a substrate, methods, and apparatus for inkless printing on reimageable paper. The document discloses an inkless reimagable paper or image forming medium formed using a composition that is imagable and erasable by heat and light, such as comprising as a photochromic material a spiropyran compound having a conjugated pathway, dispersed in a polymeric binder, wherein the photochromic material exhibits a reversible transition between a colorless state and a colored state in response to heat and light.

U.S. Patent application no. 2006251988 discloses an image forming medium including at least a polymer and a photochromic compound such as spiropyran embedded in the polymer, wherein spiropyran molecules of the spiropyran compound are chelated by a cation. The document also discloses a method of manufacturing an image forming medium comprising, dissolving an amount of a photochromic compound, which contains chelating groups, in a solvent; adding a salt, which chelates the photochromic compound, to the solvent; adding a polymer to the solvent; and mixing the solvent until the photochromic compound and the polymer are dissolved in the solvent, then providing a substrate; providing a layer of the mixed solvent on a first surface of the substrate; drying the substrate; and providing a background on a second surface of the substrate opposite the first surface, wherein the solvent comprises approximately 10% polyvinyl alcohol and approximately 2-5% ethanol in distilled water.

European patent no. 2832767 discloses a method for preparing covalent organic frameworks (COFs) and uses of the obtained COFs in the coating surfaces, ink-jet printing, spray deposition, material encapsulation and coordination chemistry.

Consequently, there is an urgent need in the art for a suitable photochromic material which can fulfill all the above mentioned requirements and can be used for practical applications in inkless and erasable printing media thereby making the recycling paper industry greener and environmentally cleaner.

OBJECTS OF THE INVENTION

The main objective of the present invention is therefore to provide photochromic metal organic frameworks (MOFs) which retain the photogenerated colour for a prolonged period of time so that the printed content remains legible/readable for reasonable time and which allows the reversibility of the colour change so that the same paper can be used for multiple cycles and also does not interfere with the paper contents.

Another objective of the present invention is to provide a process for the preparation of the photochromic metal organic frameworks which have wide applications in inkless and erasable printing.

Yet another objective of the invention to provide a printing process that will use no ink for printing and will not contaminate the environment.

SUMMARY OF THE INVENTION

The present invention provides a porous metal organic framework (MOF) comprising photochromic 1,4,5,8-naphthalenediimide (NDI) core and a metal ion, wherein the metal ion is in co-ordination with the four carboxylate groups of an organic ligand.

In a preferred embodiment, the metal ion is selected from Mg or Sr.

In a preferred embodiment, the organic ligand is a BINDI ligand.

In another embodiment, the present invention provides a process for preparation of a porous metal organic framework (MOF), the process comprises solvothermal reaction between an organic BINDI linker (N,N'-bis(5-isophthalic acid)naphthalenediimide) and corresponding metal salt in presence of a suitable solvent.

In a preferred embodiment, the solvent is a mixture of dimethylformamide (DMF) and hydrochloric acid.

In a preferred embodiment, the process further comprises removal of the solvent to obtain crystalline MOF.

In a preferred embodiment, the removal of the solvent is done by keeping the solution in hot air oven at 90° C. for 36 h.

In yet another embodiment, the present invention provides a process for inkless and erasable printing, the process comprising:
a) making fine powder of the metal organic framework (MOF) and suspending in an organic solvent;
b) providing a substrate;
c) applying the suspension of finely powdered MOF on the surface of the substrate followed by drying thereof to obtain a coating on the substrate;
d) providing a stencil followed by printing contents thereof on the coated substrate of step (c) by controlling incidence of sunlight.

In a preferred embodiment, the process of applying comprises coating over the substrate or impregnating into the substrate.

In a preferred embodiment, the substrate is selected from plastic substrate or paper substrate.

In a preferred embodiment, the printing is stable for 24 hrs.

In a preferred embodiment, the organic solvent is an alcohol.

In a preferred embodiment, the alcohol is selected from ethanol.

In a preferred embodiment, the drying of the coated substrate is done by leaving the substrate under vacuum for 15 min.

BRIEF DESCRIPTION OF THE ACCOMPANYING DRAWINGS

FIG. 1: (a) Chemical diagram of $H_4$BINDI ligand; crystal structure for (b) Mg-NDI, (c) Ca-NDI and (d) Sr-NDI. Mg-NDI shows 3D structure while for the other cases; two nets interpenetrate forming a two-fold interpenetrated structure.

Figure 2:
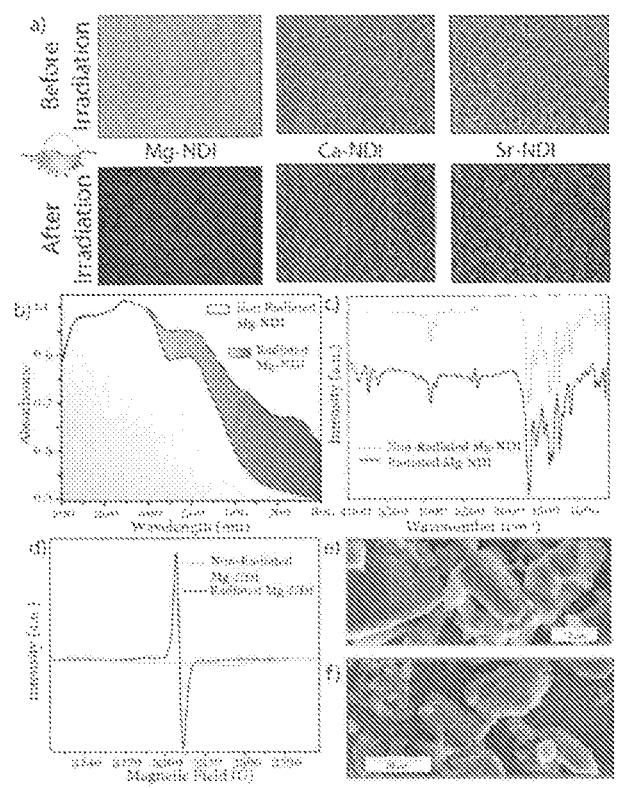

FIG. 2: (a) Colour changes of pristine MOF materials under sunlight irradiation showing photochromic property; change in (b) UV-vis spectra, (c) IR spectra (d) EPR spectrum, and SEM image (e) before and (f) after sunlight irradiation on Mg-NDI.

Figure 3:
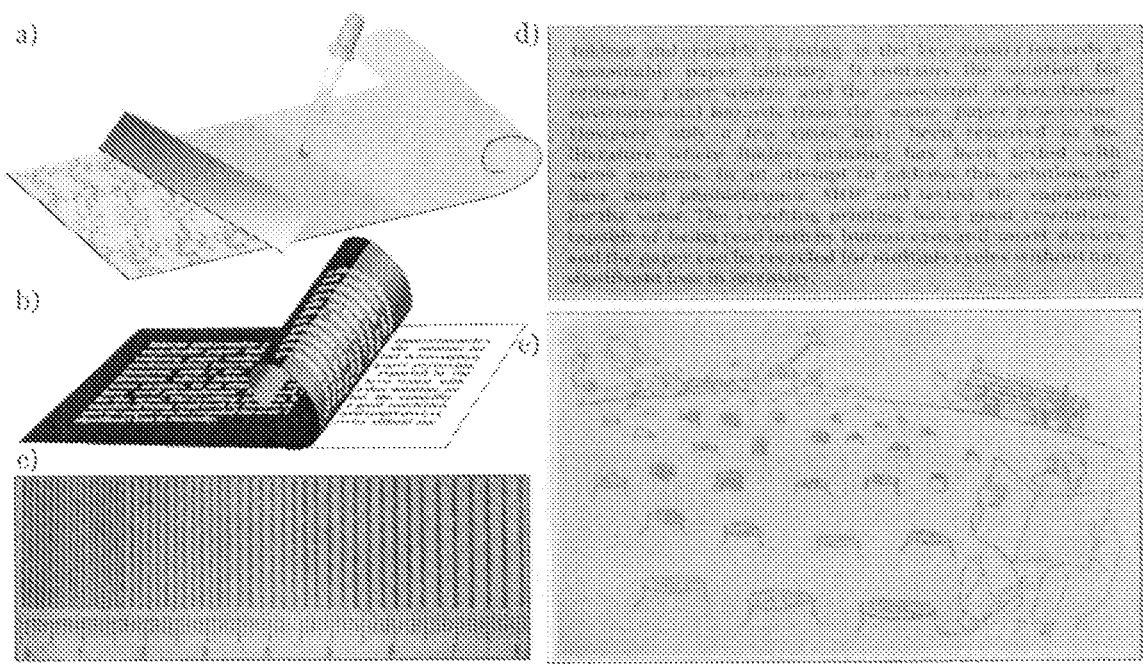

FIG. 3: (a) Schematic representation for preparation of Mg-NDI coated paper; (b) scheme for printing on the coated paper with stencil and sunlight; (c) test for resolution of the printed content by line separation; (d) printing of letters and (e) image on the Mg-NDI coated paper.

Figure 4:
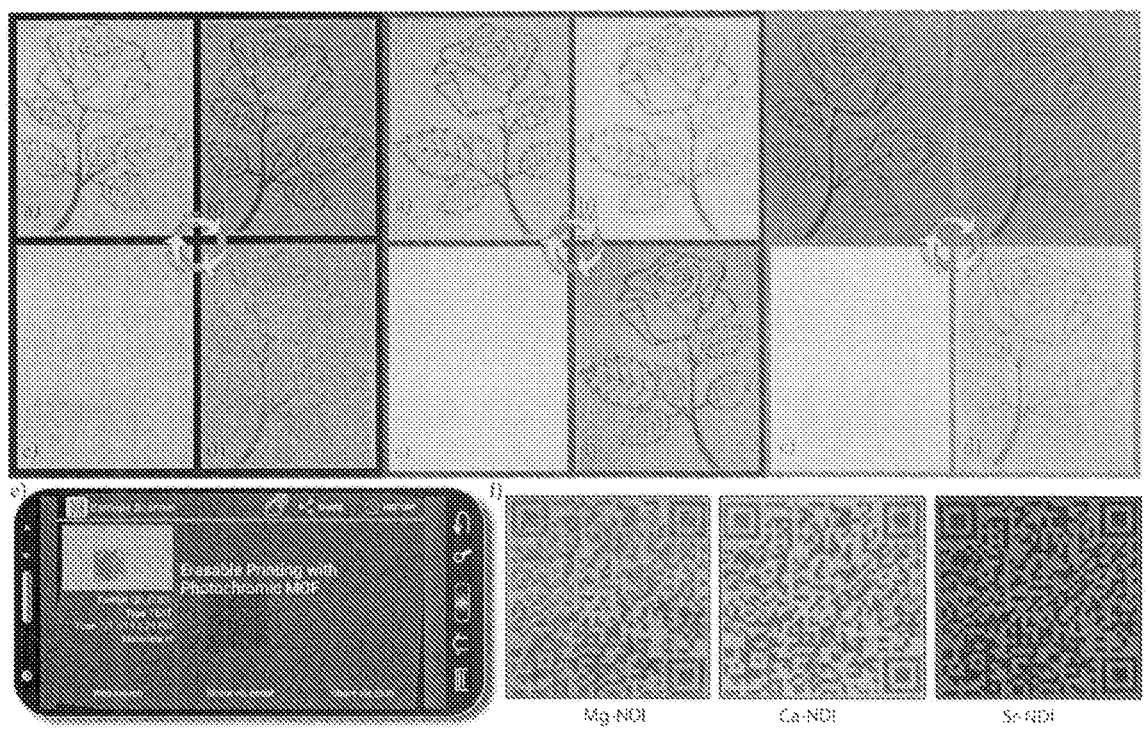

FIG. 4: (a) Photograph of a content printed on Mg-NDI/Ca-NDI/Sr-NDI coated paper; (b) content after 12 h of printing; (c) self erased paper after keeping in the dark for 24 h; (d) photograph of the paper after printing for $4^{th}$ round; (e) Detection of a QR code printed on the Mg-NDI coated paper with a smartphone; (f) QR code printed on Ca-NDI, Sr-NDI coated paper showing different coloured printing.

Figure 5:
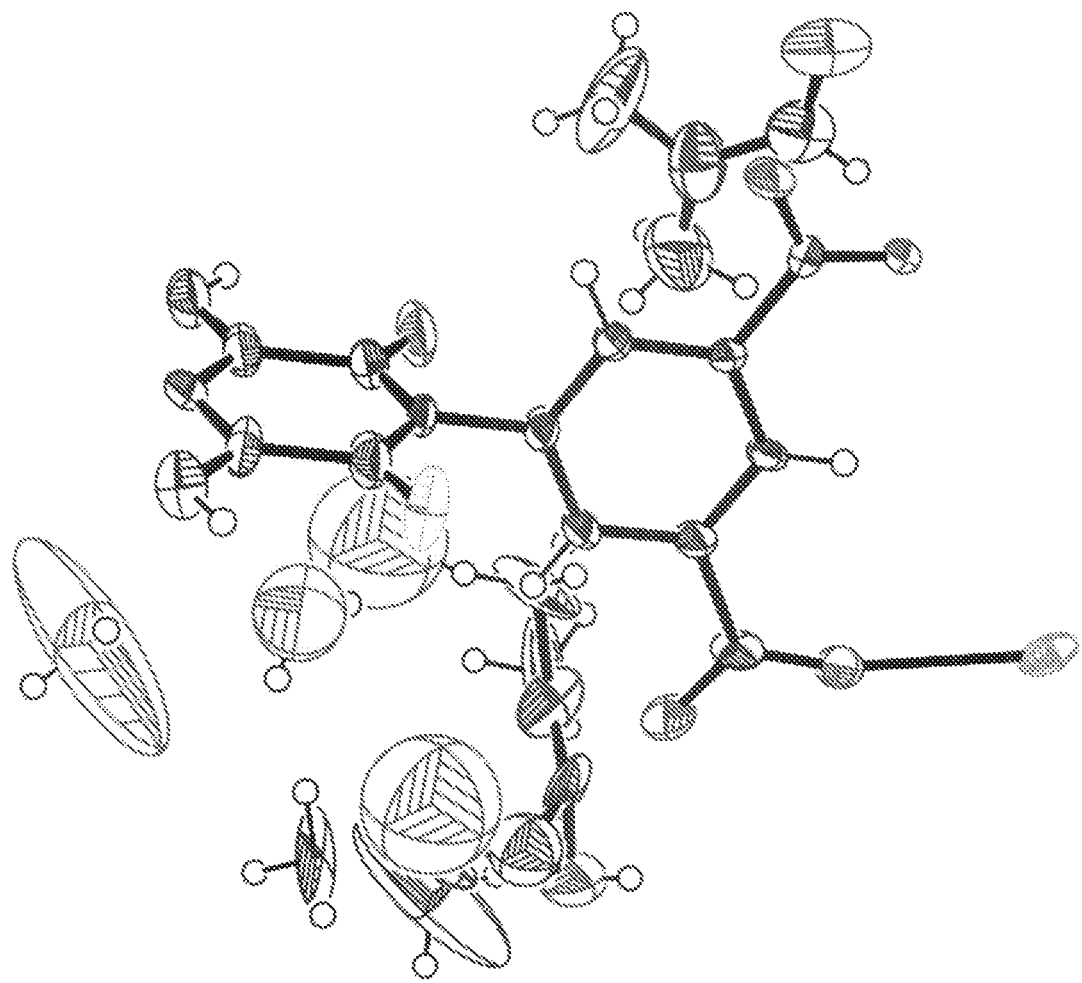

FIG. 5: ORTEP drawing of Sr-NDI. Thermal ellipsoids set to 50% probability level.

Figure 6:
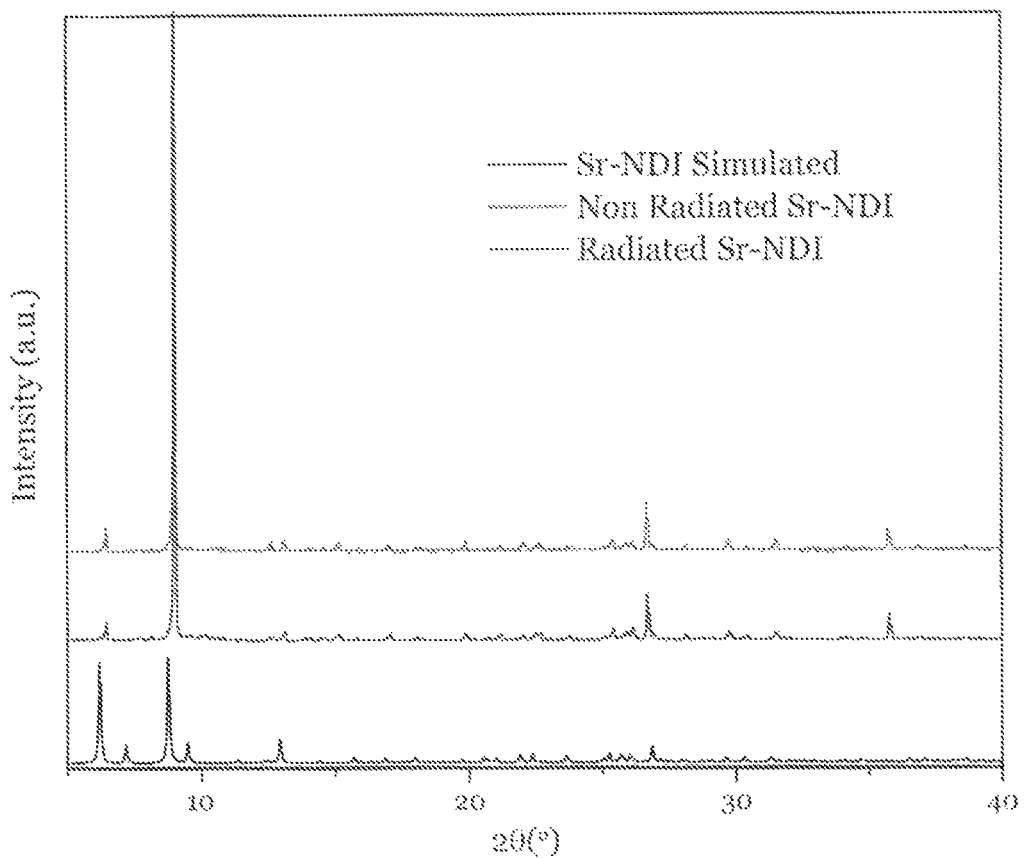

FIG. 6: PXRD pattern of Sr-NDI from As-synthesized state (Red) and Radiated State (Blue).

Figure 7:
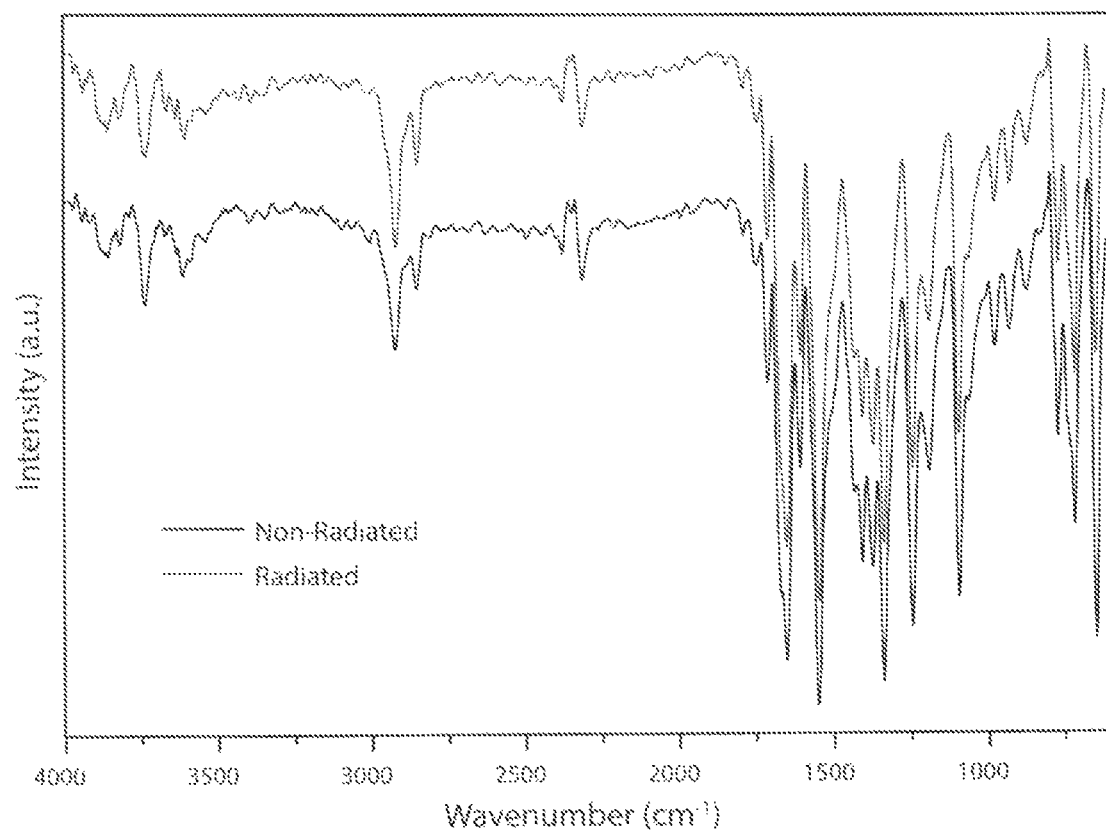

FIG. 7: Change in FT-IR spectra of Sr-NDI because of sunlight irradiation.

Figure 8:
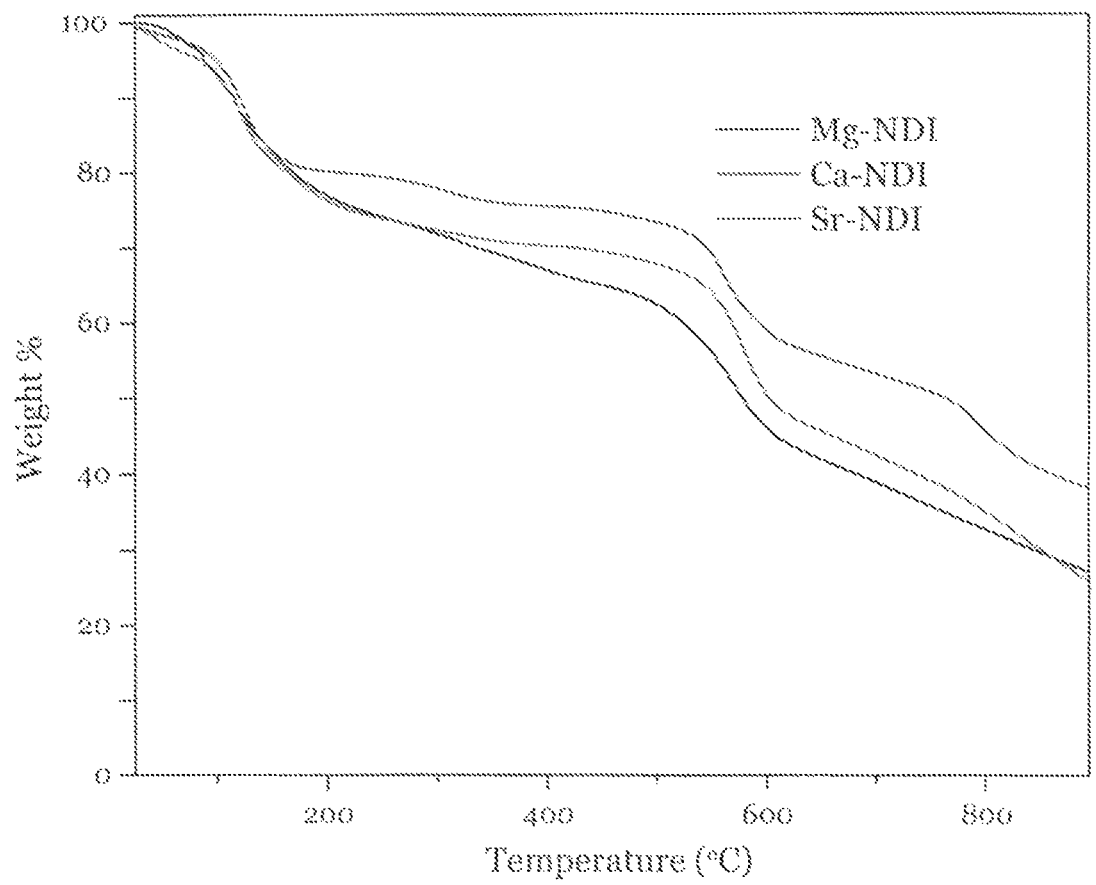

FIG. 8: TGA plots of the MOFs showing their thermal stability.

Figure 9:
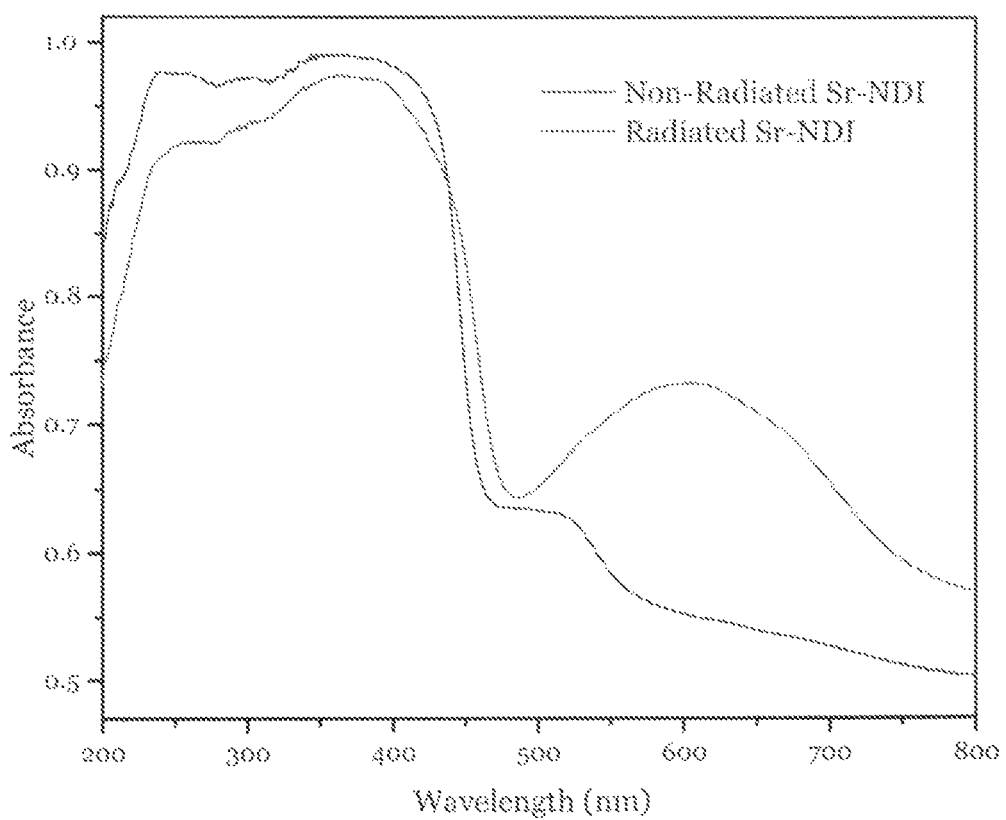

FIG. 9: UV-vis spectra of Non-Radiated and Radiated Sr-NDI showing generation of new peak centered at 605 nm because of sunlight irradiation.

Figure 10:
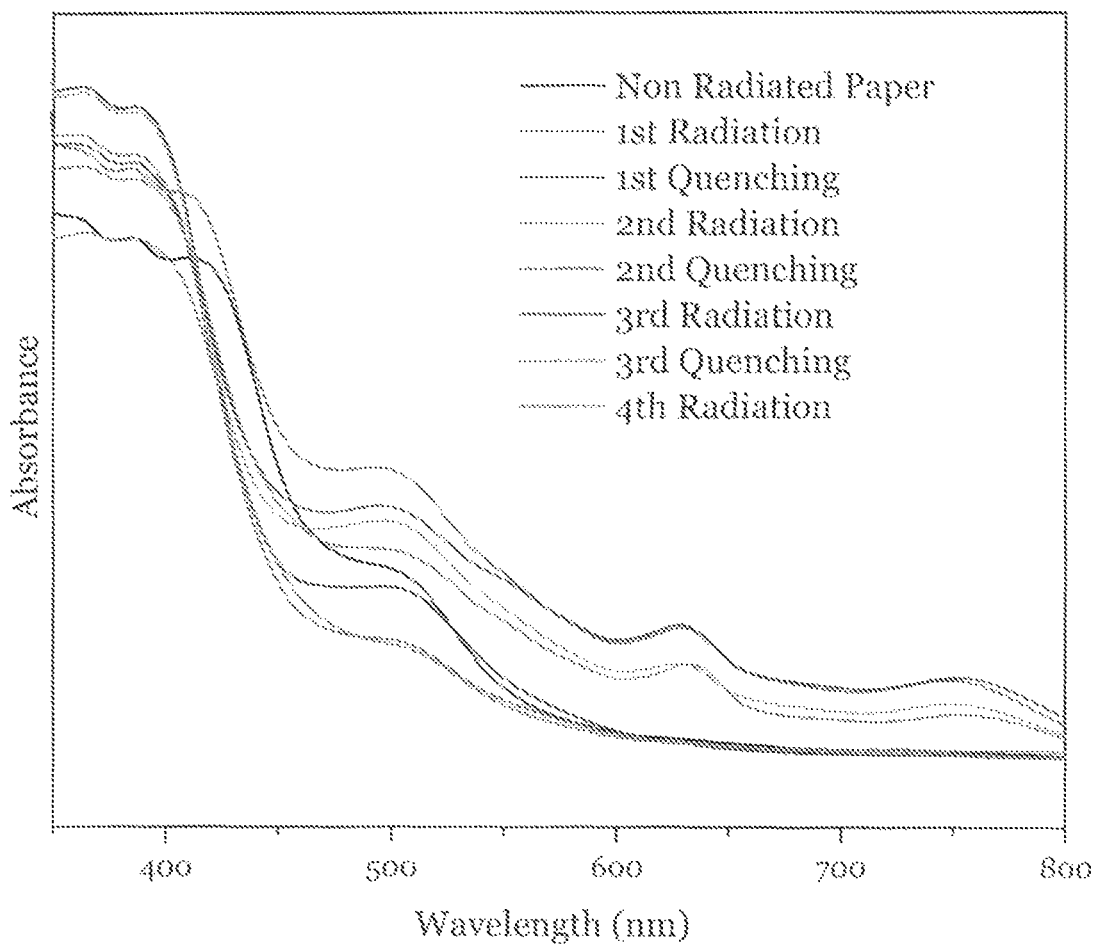

FIG. 10: UV-vis study of Mg-NDI coated paper over consecutive cycles, showing good reversibility in each cycles.

Figure 11:
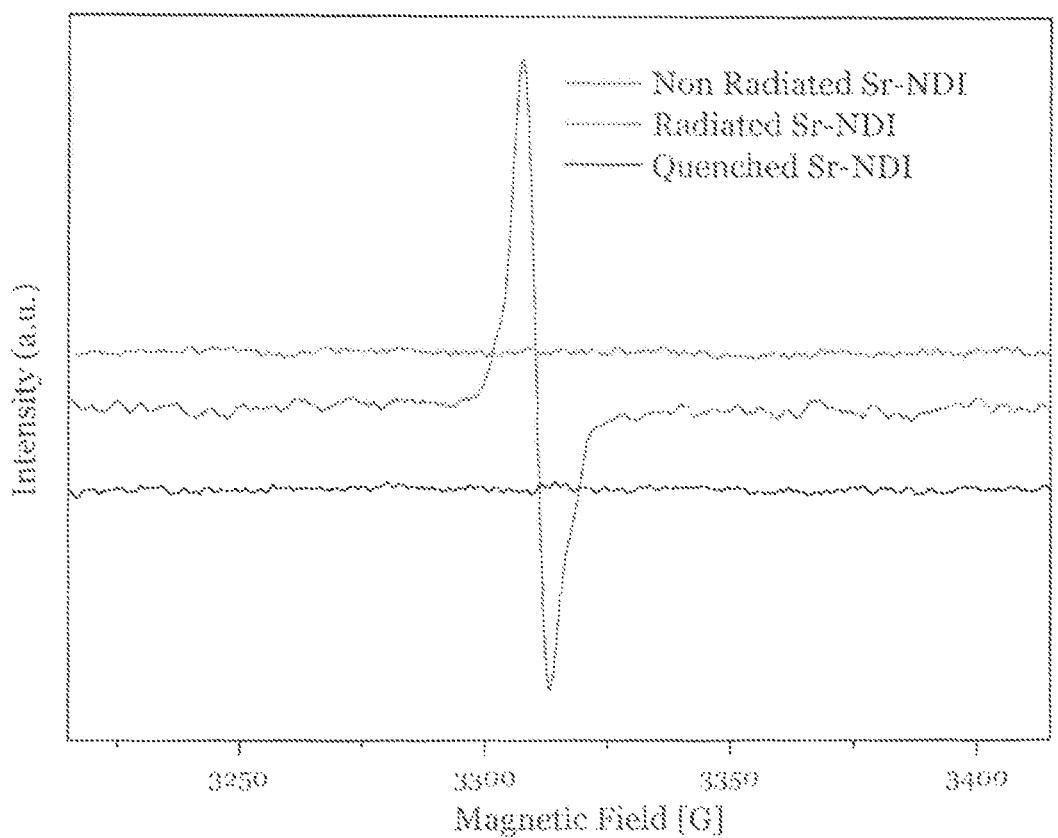

FIG. 11: EPR spectra for Sr-NDI MOF showing generation of radical species because of sunlight irradiation and subsequent quenching in dark.

Figure 12:
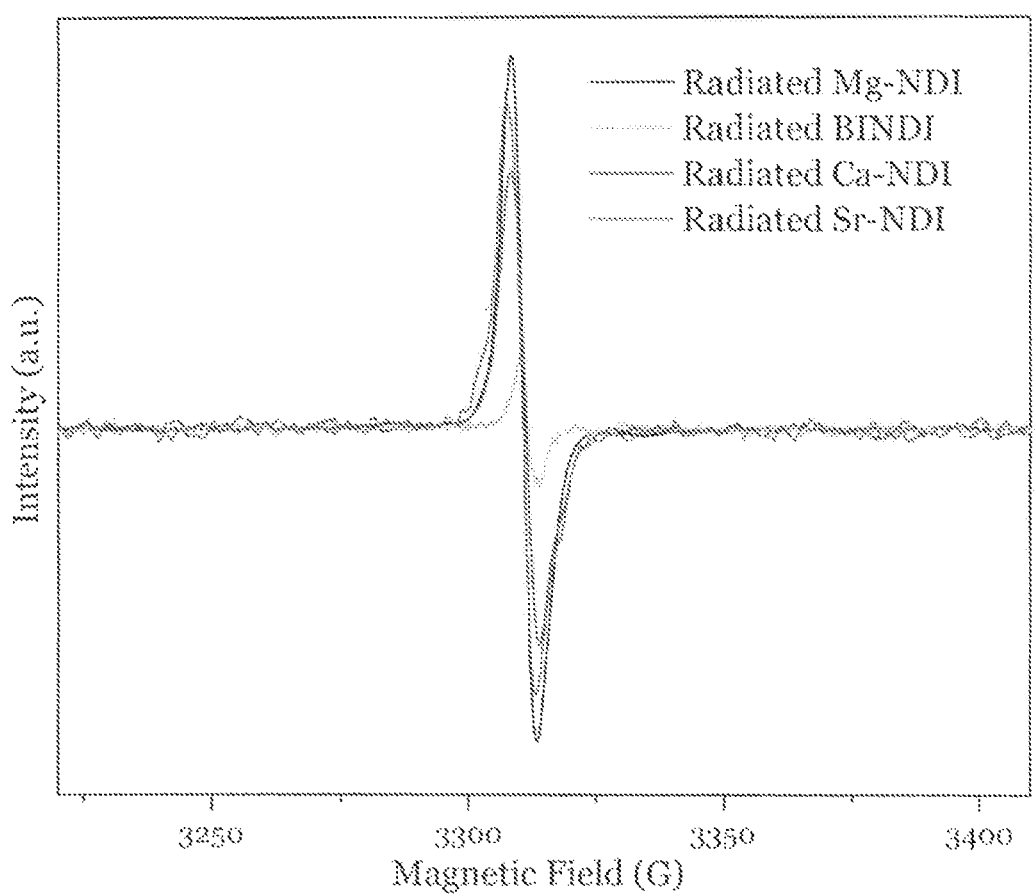

FIG. 12: Comparison of all the EPR spectra for materials obtained after sunlight irradiation showing the same nature of the generated radical species.

FIG. 13: Colour change of free BINDI ligand under sunlight irradiation showing low contrast. The colour mostly reverts back to the original colour within a short period of time.

FIG. 14: Detection of 1D barcode printed on Mg-NDI coated paper with a smartphone.

DETAILED DESCRIPTION OF THE INVENTION

The invention will now be described in detail in connection with certain preferred and optional embodiments, so that various aspects thereof may be more fully understood and appreciated.

The present invention provides metal organic frameworks (MOFs) containing photochromic 1,4,5,8-naphthalenediimide (NDI) core and metal ions selected from Mg or Sr for inkless and erasable printing.

In one embodiment, the present invention provides a porous metal organic framework (MOF) comprising photochromic 1,4,5,8-naphthalenediimide (NDI) core and metal ion, wherein metal ions are in co-ordination with the four carboxylate groups of the organic ligand.

In a preferred embodiment, the metal ion is selected from magnesium (Mg) or strontium (Sr) metals.

In another preferred embodiment, the porous metal organic framework (MOF) of the instant invention is Mg-NDI and Sr-NDI.

The 1,4,5,8-naphthalenediimide has a redox active core and can exhibit photochromic behaviour when substituted with suitable substituents. However, photochromic NDI derivatives reported in the literature show very fast loss of photogenerated colour and thus the system becomes inappropriate for the applications such as inkless printing.

Therefore, to avoid this fast decolouration, the present invention provides metal organic frameworks (MOFs) containing photochromic 1,4,5,8-naphthalenediimide (NDI) core by incorporating NDI core inside the three-dimensional extended structure of MOFs. Due to the formation of the extended structures and the additional interactions, the photochromic behaviour of the NDI core in the MOF changes abruptly as compared to the discrete NDI units that makes it suitable for the inkless printing media.

In an embodiment, the present invention provides a process for synthesis of metal organic frameworks (MOFs) containing photochromic 1,4,5,8-naphthalenediimide (NDI) cores comprising Mg or Sr metals.

In a typical reaction, BINDI ligand and the corresponding metal ions salt are dissolved in a mixture of DMF and 3N HCl. The solution is kept in a hot air oven at 90° C. for 36 h to obtain crystalline MOFs. These MOF crystals are washed with anhydrous DMF, followed by absolute ethanol and used for further characterization/applications.

Accordingly, all the MOFs were synthesized by the solvothermal reactions between the organic BINDI linker (N,N'-bis(5-isophthalic acid)naphthalenediimide) (FIG. 1a) and the corresponding metal salts. All these MOFs have 3D extended structure (as shown in FIGS. 1b, 1c, 1d) where metal ions are in co-ordination with the four carboxylate groups of the organic ligand.

According to crystallization studies it has been observed that Mg-NDI, crystallizes in P2/c space group with two different types of co-ordination environment around the Mg(II) centers. Such co-ordination makes the parallel orientated NDI moieties separated by a distance of 7.1 Å. Further, it has been observed that rectangular shaped channels [10.9×7.1 Å$^2$] inside the Mg-NDI structure and the wall of these channels are constructed from NDI moieties. However, Ca- and Sr-NDI crystallize in I4$_1$/a space group and differ structurally from Mg-NDI. Both Ca- and Sr-NDI are isostructural and in the extended framework, two equivalent nets are interlocked via π-π stacking between adjacent NDI moieties forming a 2-fold interpenetrated structure (FIGS. 1c, 1d), which shows that the NDI moieties of the 2nd net align in a perpendicular orientation compared to the 1st net, during the interpenetration. On perusing the PXRD patterns of the as-synthesized MOFs, it is observed that PXRD patterns match well with the simulated patterns derived from the corresponding MOF crystal structure, accounting for the bulk phase purity of the as-synthesized materials (FIG. 6). In a further embodiment, FT-IR analysis of the MOFs shows that additional peaks appear at 2918 and 2846 cm$^{-1}$ in comparison to free ligand; corresponding to the formation of new M-O bonds.

The TGA plots show that the as-synthesized MOFs contain weakly co-ordinating solvent molecules inside their cavity. For example, as evidenced from the TGA plots, these co-ordinating solvents present in the Mg-NDI framework are released around at 150° C. temperature, (resulting in 17% weight loss) of the dried MOF samples and the frameworks eventually decompose at 550° C. (FIG. 8).

In a further embodiment, the colour of the Mg-NDI is observed to be light yellow while the other MOFs are found to be almost colourless. The photochromic nature of these MOFs is confirmed by exposing dried MOF crystals to intense sunlight. When exposed to intense sunlight, a sweeping colour change occurred for all these MOFs, confirming their photochromic nature (FIG. 2a). The colour of these irradiated materials is found to be dependent on the structure of the parent MOF. Mg-NDI turned into brownish black colour after the sunlight irradiation for 60 seconds, while the isostructural Ca-NDI and Sr-NDI MOFs turned into green colour after similar treatment. This colour change causes the generation of new additional peaks in the UV-vis spectra for radiated samples [630 and 740 nm centered broad peak for Mg-NDI, FIG. 2b; 620 and 605 nm centered peak for Ca- and Sr-NDI, respectively; FIG. 9]. Further, the PXRD patterns (FIG. 6) of these MOFs indicate that they retain their initial structure even after the photochromic transformation and corresponding relaxation. FT-IR spectra of all the MOFs are also found to be identical for the cases of non-radiated, radiated and relaxed materials, again suggesting the retention of functional groups and the bonding during this photochromic changes (FIG. 2c). Apart from the internal structure, the external morphology of Mg-NDI is also retained after sunlight irradiation, as evidenced from the SEM images (FIGS. 2e and 2f).

It is reported in the literature that due to the n-type character, under suitable conditions each NDI moiety undergoes one electron transfer and gets converted into a NDI radical species (NDI.). This NDI. radical is generated from neutral NDI via various methods like chemical, photochemical and electrochemical treatment. NDI˙ bears a characteristic EPR signal at g=2.002-2.004 region, originating from the unpaired electron. This unpaired electron from NDI˙ gets quenched readily when comes in contact with paramagnetic species like oxygen (O2) gas. Use of alkaline earth metal ions as nodes for construction of Mg-NDI, Ca-NDI and Sr-NDI keep the unpaired electron of the radical species unaffected due to the absence of partially filled d-orbital. EPR studies revealed that as-synthesized MOFs are silent to the applied magnetic field while a sharp singlet peak appearing for the case of sunlight radiated MOFs with g=2.003 (FIG. 2d), which suggests that the MOFs generate stable radical species when subjected to intense sunlight irradiation.

The photoirradiated dark brown coloured Mg-NDI shows a sharp EPR signal at g=2.003, which is absent for the as-synthesized MOFs. This signal indicates the formation of NDI˙ radical species and vanishes when the materials are quenched and returned to their original colour. It is further observed that after sunlight irradiation BINDI ligand also shows similar signal [g=2.004, FIG. 12] in the EPR spectrum; indicating the generation of NDI˙ species in its structural backbone. However, this radical generation requires a prolonged irradiation time [10 min] followed by quick loss of photogenerated colour [reverts to original colour in <2 h, FIG. 13], indicating a short lifetime [compared to 12 h for Mg-NDI] for the generated radical species. It is found that the colour of the radiated material has a poor contrast compared to the non-radiated one, thus making BINDI non-suitable for inkless and erasable printing applications. This short lifetime of the BINDI radical species is a result of short π-π stacked NDI cores, which are located at a separating distance of 2.6 Å, as evidenced from its crystal structure. The stacking between the adjacent NDI cores facilitates the quenching of NDI˙ through the transfer of electrons to the neighbouring moieties and as a result, the photogenerated colour becomes transient and quickly reverts to its initial colour. Surprisingly, in all the MOFs reported in the present invention, these NDI cores are separated by a distance of ~7.1 Å which eliminates the chance of π-π stacking among those moieties and brings stability to the NDI˙ radical species. In case of isostructural Ca- and Sr-NDI MOFs, the π-π stacking distance between the adjacent NDI moieties is 2.4 Å. However their orientation is orthogonal to each other and hence, the radicals cannot be quenched via transport mechanism as it happens in the bare BINDI ligand. Thus the photogenerated NDI˙ within the MOF backbone attains stability. The nature of the photogenerated radical [singlet peaks centered at g=2.003] was found to be same for all the MOFs (FIG. 13) and bare BINDI ligand. Incorporation of the NDI moieties inside MOF structure helps to enhance the retention time [from <2 h for bare BINDI linker to >12 h for MOFs] of the photogenerated radical species and the corresponding colour of the resulting material.

In one embodiment, the present invention provides metal organic frameworks (MOFs) containing photochromic 1,4,5,8-naphthalenediimide (NDI) core for inkless and erasable printing.

In another embodiment, the present invention provides a process for inkless and erasable printing using the prepared metal organic framework (MOF) wherein said process comprising the steps of:
a) Making fine powder of the metal organic framework and suspending in ethanol;
b) Simultaneously, providing a substrate;
c) Providing a coating the ethanol suspension of finely powdered MOF on the surface of the substrate;
d) Drying the substrate under vacuum; and
e) Providing stencil followed by printing the contents on coated paper of step (d) by controlling the incidence of sunlight.

In a preferred embodiment, the metal organic framework (MOF) is selected from Mg-NDI and Sr-NDI.

In another preferred embodiment, the process of applying comprises coating over the substrate or impregnating into the substrate.

In yet another preferred embodiment, the substrate is selected from plastic substrate or paper substrate.

In still another preferred embodiment, the drying of substrate comprises leaving the substrate under vacuum for 15 min.

In yet another preferred embodiment, said printing is stable for 24 hrs.

The NDI based MOFs provided according to the invention have been employed as inkless and erasable printing media. In accordance with this embodiment, the as-synthesized Mg-NDI is immersed in ethanol for 24 h prior to be coated on to a paper. The MOF coated paper is prepared by drop casting an ethanol suspension of finely powdered Mg-NDI on a cellulose filter paper followed by surface smoothening with a glass slide (FIG. 3a). The paper is then dried under vacuum so as to allow the coating material to adhere to the paper, without losing the flexible nature of the resulting coated paper. The printing of the contents on this coated paper is performed by controlling the incidence of sunlight through a stencil. The stencil is prepared by printing an inverted object of the desired content on a transparent polyurethane sheet. The printing surface of the coated paper is then covered with the stencil and the assembly is kept in the intense sunlight for less than 60 seconds. After this exposure, the stencil is removed from the top of the coated paper to obtain the content printed in brownish black colour on pale yellow background of Mg-NDI (FIG. 3b). The resolution test for the printing suggested that parallel lines having width of 1.0 mm, separated by a distance of 0.5 mm are successfully resolved without any difficulty (FIG. 3c). Large scale text printing is tested with a stencil of 11.9×5.4 cm$^2$ sized print obtained with a similarly designed stencil. No overlap among the 610 characters occupied in 10 lines is observed and each of the characters is clearly distinguishable from its next neighbour (FIG. 3d). The colour contrast between the foreground and background is found to be well enough for visual reading of the content. This visual legibility is again confirmed from an outline sketch having dimension of 11.5×6.5 cm$^2$. The objects present in the drawing are well-defined in respect to their constituent lines and the printed content is easily visualized (FIG. 3e). Similarly, the printing with Ca- and Sr-NDI coated paper gives excellent legibility where the resulting content is printed in dark green colour.

It is observed that printed content disappears into the background after 24 h, converting it into a blank paper which can be used for next round of printing as shown in FIG. 4d. It has also been observed that the intensity of the 4$^{th}$ round printed content remains the same as that of the 1$^{st}$ round. As the printed content is kept in ambient atmosphere, aerial oxygen diffuses through the excited material converting it back into the initial state. Time required for complete relaxation of the excited material along with complete reversal to the initial colour was found to be nearly 24 h.

Thus the printed content remained legible for long period of time (FIG. 4c), which indicates the sufficiency of the same for temporary printing uses.

In yet another embodiment, it is demonstrated that the erasing of the printed paper can be accelerated for re-use within 24 h period which can be accomplished by flushing oxygen gas on the printed paper. This aspect also conclusively proves the reversibility and recyclability of the printing media.

In a further embodiment, machine legible nature of the printed content on the Mg-NDI coated paper has been studied to establish the legibility of the printed content/the resolution to be recognized by smart devices apart from the naked eye legibility of the printed content. To establish this, 1D and 2D barcodes are printed on the Mg-, Ca- and Sr-NDI coated papers using an identical stencil, to confirm the ability to be decoded by smart devices. A version-5 QR code (containing 37 rows and 37 columns) with a dimension of 4.7×4.7 cm$^2$ is prepared which contained 39 characters (FIG. 4f). The embedded code 'Erasable Printing with Photochromic MOF' is readily decoded with any reader software installed on smart electronic devices, as shown in FIG. 4e. Similar quick response is also found for the case of 1D barcodes (FIG. 14), proving the excellent machine legible nature of the printed content on the Mg-NDI coated paper. UV-vis study of the printed and erased papers over multiple cycles (FIG. 10) showed that the colour intensity of Mg-NDI in both coloured and colourless form holds steady for 04 cycles.

Thus in a nut shell, the present invention successfully demonstrated a novel approach to develop an inkless and erasable printing medium using photochromic MOFs. Precise impression of the desired content on the printing medium has been achieved by controlling the incidence of sunlight on the medium with a stencil and without use of any ink. Further, it has been demonstrated that the resulting print is well-recognized by smart electronic devices as well. The printed content is self-erased after 24 h, without using any other external stimuli like heat, or UV light. The self-erasing nature makes the system suitable for performing several printing-erasing cycles with the same paper, making the printing process cost-effective and environmental friendly. The invention further establishes that the early and accelerated erasing of printed paper can also be achieved by flushing oxygen gas on the printed paper. The present invention further demonstrates that it is easier to tune the colour of printing by selection of different MOFs, having different structures. Development of new materials capable of showing multicolour-photochromic behaviour for application in colour printing is possible with the help of the disclosure provided herein above in the specification to achieve the desired success.

EXAMPLES

The following examples, which include preferred embodiments, will serve to illustrate the practice of this invention, and therefore should not be construed to limit the scope of the invention in any manner.

Materials and Methods

All the reagents are commercially available and used as received without any further purification. Single Crystal X-Ray Diffraction data were collected on a Super Nova Dual source X-ray Diffractometer system (Agilent Technologies) equipped with a CCD area detector. Powder X-ray diffraction (PXRD) patterns were recorded on a Rigaku Smartlab diffractometer for Cu K$_\alpha$ radiation ($\lambda$=1.5406 Å), with a scan speed of 2° min$^{-1}$ and a step size of 0.02° in 2θ. Fourier transform infrared (FT-IR) spectra were recorded on a Bruker Optics ALPHA-E spectrometer with a universal Zn—Se ATR (attenuated total reflection) accessory in the 600-4000 cm$^{-1}$ wavenumber region. Thermo-gravimetric analyses (TGA) were carried out on a SDT Q600 TG-DTA analyser under N$_2$ atmosphere at a heating rate of 10° C. min$^{-1}$ within the temperature range of 30-900° C. Solid state UV-vis absorbance studies were carried out with a Agilent make UV-vis-NIR spectrophotometer. EPR measurements were performed with a Bruker instrument under ambient condition.

Example 1: Synthesis of BINDI Ligand and Metal Organic Framework (Scheme 1)

N,N'-bis(5-isophthalic acid)naphthalenediimide (H$_4$BINDI) was synthesized following a previously reported procedure in the literature. 1,4,5,8-naphthalene-tetracarboxylic acid dianhydride (6.70 g, 25.0 mmol) was taken into a 250 mL round bottomed flask and suspended in 125 mL acetic acid. The mixture was stirred for 10 min. To this solution, 5-aminoisophthalic acid (9.05 g, 50.0 mmol) was added and the resulting suspension was allowed to reflux for 12 h. The reaction was cooled down to room temperature and 100 mL of water was added to precipitate the product. The resultant product was collected by filtration and washed with ethanol. The obtained solid was dried in vacuum to yield 12.0 g of off-white solid (isolated yield=12.0 g, 77%). The compound was recrystallized from DMF as an off-yellow material (isolated yield=10.5 g, 67%).

Scheme 1

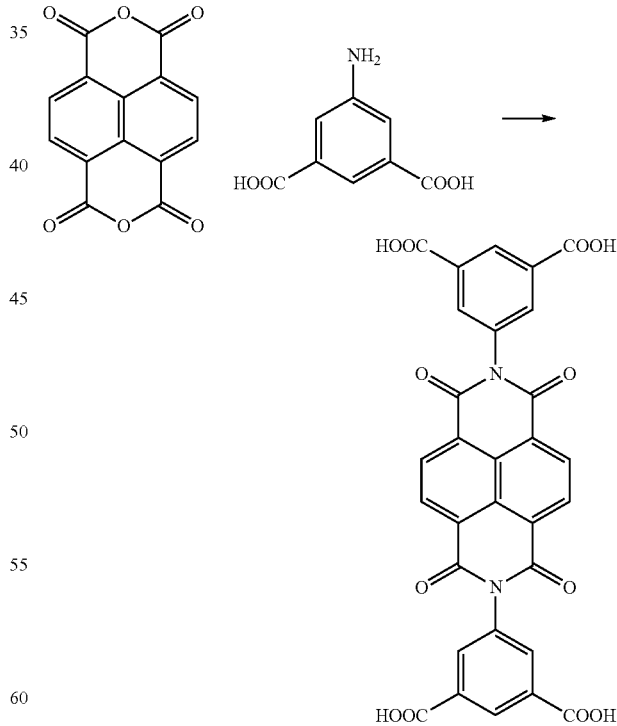

Example 2: Synthesis of Sr-NDI

The needle shaped crystals of Sr-NDI MOF were synthesized by reacting N,N'-bis(5-isophthalic acid)naphthalenediimide (H₄BINDI) (21 mg, 0.035 mmol) with Sr(NO₃)₂ (24 mg, 0.093 mmol) in 4 mL DMF and 0.2 mL HCl (3 N) at 90° C. for 24 h. Needle shaped colourless crystals were collected from the reaction vial and washed with dry DMF and preserved for further applications and characterizations.

Example 3: Synthesis of Mg-NDI

Mg-NDI were also synthesized following the same reaction protocol. In a typical reaction, 21 mg (0.03 mmol) of BINDI ligand and 24 mg (0.09 mmol) of Mg(NO₃)₂.6H₂O were reacted in a mixture of 4 mL DMF and 0.2 mL of 3N HCl at 90° C. for 36 h. The plate like crystals, thus obtained were then collected and washed with DMF.

Example 4 (Comparative Example): Synthesis of Ca-NDI

Ca-NDI were also synthesized following the same reaction protocol. Block shaped Ca-NDI crystals were readily obtained through a similar reaction between 21 mg (0.035 mmol) BINDI and 21 mg (0.09 mmol) Ca(NO₃)₂.4H₂O in a solvent mixture of 4 mL DMF and 0.2 mL of 3N HCl at 90° C. for 36 h in an hot air oven. The block shaped crystals were then washed with anhydrous DMF and stored for further usages.

Example 5: Single Crystal XRD and Crystal Structure of Sr-NDI

As synthesized crystals of Sr-NDI were placed inside a glass (Hampton research) and then mounted in the diffractometer. The data collection was done at 200 K. The crystals were mounted on a Super Nova Dual source X-ray Diffractometer system (Agilent Technologies) equipped with a CCD area detector and operated at 250 W power (50 kV, 0.8 mA) to generate Mo Kα radiation ($\lambda$=0.71073 Å) and Cu Kα radiation ($\lambda$=1.54178 Å) at 298(2) K. Initial scans of each specimen were performed to obtain preliminary unit cell parameters and to assess the mosaicity (breadth of spots between frames) of the crystal to select the required frame width for data collection. CrysAlisPro program software suite was used to carry out overlapping φ and ω scans at detector (2θ) settings (2θ=28). Following data collection, reflections were sampled from all regions of the Ewald sphere to re-determine unit cell parameters for data integration. In no data collection was evidence for crystal decay encountered. Following exhaustive review of collected frames the resolution of the data set was judged. Data were integrated using CrysAlisPro software with a narrow frame algorithm. Data were subsequently corrected for absorption by the program SCALE3 ABSPACK scaling algorithm.

These structures were solved by direct method and refined using the SHELXTL 97 software suite. Atoms were located from iterative examination of difference F-maps following least squares refinements of the earlier models. Final model was refined anisotropically (if the number of data permitted) until full convergence was achieved. Hydrogen atoms were placed in calculated positions (C-H=0.93 Å) and included as riding atoms with isotropic displacement parameters 1.2-1.5 times Ueq of the attached C atoms. In some cases, modelling of electron density within the voids of the frameworks did not lead to identification of recognizable solvent molecules in these structures, probably due to the highly disordered contents of the large pores in the frameworks. Highly porous crystals that contain solvent-filled pores often yield raw data where observed strong (high intensity) scattering becomes limited to ~1.0 Å at best, with higher resolution data present at low intensity. A common strategy for improving X-ray data, increasing the exposure time of the crystal to X-rays, did not improve the quality of the high angle data in this case, as the intensity from low angle data saturated the detector and minimal improvement in the high angle data was achieved. Additionally, diffused scattering from the highly disordered solvent within the void spaces of the framework and from the capillary to mount the crystal contributes to the background and the 'washing out' of the weaker data. Electron density within void spaces has not been assigned to any guest entity but has been modelled as isolated oxygen and/or carbon atoms. The foremost errors in all the models are thought to lie in the assignment of guest electron density. The structure was examined using the ADSYM subroutine of PLATON to assure that no additional symmetry could be applied to the models. The ellipsoids in ORTEP diagrams are displayed at the 50% probability level unless noted otherwise (FIG. 5).

TABLE 1

Crystal data and structure refinement for Sr-NDI

| | |
|---|---|
| Identification code | Sr-NDI |
| Empirical formula | C44 H44 N4 O23 Sr2 |
| Formula weight | 1172.07 |
| Temperature/K | 200.01(2) |
| Crystal system | tetragonal |
| Space group | I 41/a |
| a/Å | 28.4784(7) |
| b/Å | 28.4784(7) |
| c/Å | 13.6334(4) |
| α/° | 90.00 |
| β/° | 90.00 |
| γ/° | 90.00 |
| Volume/Å³ | 11056.9(5) |
| Z | 8 |
| $\rho_{calc}$ mg/mm³ | 1.408 |
| m/mm⁻¹ | 0.109 |
| F(000) | 4768 |
| Crystal size/mm³ | 0.6 × 0.2 × 0.2 |
| Theta range for data collection | 3.16 to 29.08° |
| Index ranges | −30 ≤ h ≤ 38, −38 ≤ k ≤ 38, −17 ≤ l ≤ 18 |
| Reflections collected | 11940 |
| Independent reflections | 7392[R(int) = 0.0447] |
| Data/restraints/parameters | 7392/0/367 |
| Goodness-of-fit on F² | 0.930 |
| Final R indexes [I > 2σ (I)] | R₁ = 0.1393, wR₂ = 0.3624 |
| Final R indexes [all data] | R₁ = 0.1810, wR₂ = 0.3919 |
| Largest diff. peak/hole/e Å⁻³ | 2.08/−1.82 |

TABLE 2

Crystal data and structure refinement for Mg-NDI

| | |
|---|---|
| Identification code | Mg-NDI |
| Empirical formula | C₆₉H₃₅Mg₄N₇O₃₀ |
| Formula weight | 1539.28 |
| Temperature/K | 150(2) |
| Crystal system | Monoclinic |
| Space group | P2/c |
| a/Å | 34.3 |
| b/Å | 10.0 |
| c/Å | 17.7 |
| α/° | 90.00 |
| β/° | 96.23 |
| γ/° | 90.00 |
| Volume/Å³ | 6082.6(8) |
| Z | 2 |
| $\rho_{calc}$ mg/mm³ | 0.8404 |
| m/mm⁻¹ | 0.085 |
| F(000) | 1572.0 |
| Crystal size/mm³ | 0.31 × 0.25 × 0.17 |

TABLE 2-continued

Crystal data and structure refinement for Mg-NDI

| | |
|---|---|
| Theta range for data collection | 5.96 to 58.38° |
| Index ranges | $-43 \leq h \leq 47, -12 \leq k \leq 13, -24 \leq l \leq 22$ |
| Reflections collected | 34619 |
| Independent reflections | 14116[R(int) = 0.0896] |
| Data/restraints/parameters | 14116/0/506 |
| Goodness-of-fit on $F^2$ | 0.7929 |
| Final R indexes [I > 2σ (I)] | $R_1 = 0.1062, wR_2 = 0.3011$ |
| Final R indexes [all data] | $R_1 = 0.1636, wR_2 = 0.3108$ |
| Largest diff. peak/hole/e Å$^{-3}$ | 0.7875/−0.5894 |

TABLE 3

Crystal data and structure refinement for Ca-NDI (Comparative data)

| | |
|---|---|
| Identification code | Ca-NDI |
| Empirical formula | $C_{36} H_{27} Ca_2 N_4 O_{16}$ |
| Formula weight | 851.78 |
| Temperature/K | 298 |
| Crystal system | monoclinic |
| Space group | $I4_1/a$ |
| a/Å | 28.1 |
| b/Å | 28.1 |
| c/Å | 13.5 |
| α/° | 90 |
| β/° | 90 |
| γ/° | 90 |
| Volume/Å$^3$ | 10749.1(10) |
| Z | 8 |
| $\rho_{calc}$ mg/mm$^3$ | 0.165 |
| m/mm$^{-1}$ | 0.269 |
| F(000) | 3512 |
| Crystal size/mm$^3$ | 0.5 × 0.2 × 0.2 |
| 2Θ range for data collection | 6.36 to 59.16° |
| Index ranges | $-35 \leq h \leq 36, -27 \leq k \leq 37, -9 \leq l \leq 18$ |
| Reflections collected | 13531 |
| Independent reflections | 9140[R(int) = 0.2181] |
| Data/restraints/parameters | 9140/0/514 |
| Goodness-of-fit on $F^2$ | 1.532 |
| Final R indexes [I >= 2σ (I)] | $R_1 = 0.2668, wR_2 = 0.5141$ |
| Final R indexes [all data] | $R_1 = 0.3975, wR_2 = 0.5766$ |
| Largest diff. peak/hole/e Å$^{-3}$ | 0.79/−0.60 |

Example 6: Printing Method

Printing method used for this work has been demonstrated in FIG. 3. Where, a stencil was used to control the incidence of light on the MOF coated paper. Thus, a precise impression of the content was obtained on the paper without using any ink. The Reusability of the paper has been demonstrated in FIG. 4, where it has been shown that the paper can be erased after printing and subsequently can be reused again for next rounds of printing. The same reusability has been verified from the consecutive cycles of UV-vis study, as shown in FIG. 10.

Advantages of Invention

Ability to retain the photogenerated colour for a prolonged period of time so that the content remains legible/readable;

The reversibility of the colour change so that the same paper can be used for multiple cycles The intactness of the colour in presence of paper contents.

We claim:

1. A porous metal organic framework (MOF) comprising:
   BINDI (N,N'-bis(5-isophthalic acid) naphthalenediimide), and
   a metal ion selected from Mg and Sr,
   wherein the metal ion is in coordination with the four carboxylate groups of BINDI, and
   wherein said metal organic framework is useful for process for inkless and erasable printing.

2. A process for preparation of a porous metal organic framework (MOF), the process comprises solvothermal reaction between BINDI and a metal salt in the presence of a suitable solvent wherein the metal salt is selected from Mg and Sr.

3. The process as claimed in claim 2, wherein the solvent is a mixture of dimethylformamide (DMF) and hydrochloric acid.

4. The process as claimed in claim 3, further comprising of removal of the solvent to obtain crystalline MOF.

5. The process as claimed in claim 4, wherein the removal of the solvent is done by keeping the solution in hot air oven at 90° C. for 36 h.

6. A process for inkless and erasable printing, the process comprising:
   a) making fine powder of the metal organic framework (MOF) as claimed in claim 1 and suspending in an organic solvent;
   b) providing a substrate;
   c) applying the suspension of finely powdered MOF on the surface of the substrate followed by drying thereof to obtain a coating on the substrate;
   d) providing a stencil followed by printing contents thereof on the coated substrate of step (c) by controlling incidence of sunlight.

7. The process as claimed in claim 6, wherein applying comprises coating over the substrate or impregnating into the substrate.

8. The process as claimed in claim 6, wherein the substrate is selected from plastic substrate or paper substrate.

9. The process as claimed in claim 6, wherein the printing is stable for 24 hrs due to the stable photochromic MOF structures.

10. The process as claimed in claim 6, wherein the organic solvent is an alcohol.

11. The process as claimed in claim 10, wherein the alcohol is selected from ethanol.

12. The process as claimed in claim 6, wherein the drying is done by leaving the substrate under vacuum for 15 min.

* * * * *